United States Patent [19]

Brandt et al.

[11] Patent Number: 4,849,174
[45] Date of Patent: Jul. 18, 1989

[54] GAS GENERATING DEVICE

[75] Inventors: Michael D. Brandt, Chicago; Francois Mermoud, Westmont, both of Ill.

[73] Assignee: American Air Liquide, New York, N.Y.

[21] Appl. No.: 85,888

[22] Filed: Aug. 14, 1987

[51] Int. Cl.⁴ .................. G01N 7/00; A24F 25/00
[52] U.S. Cl. ........................... 422/62; 422/83; 239/34
[58] Field of Search ............... 422/112, 187, 189, 116, 422/62, 83; 239/34

[56] References Cited

U.S. PATENT DOCUMENTS

| 3,057,699 | 10/1962 | McLeod | 422/116 |
| 3,856,204 | 12/1974 | Chand | 239/34 |
| 4,399,942 | 9/1983 | Chand | 239/34 |

Primary Examiner—Barry S. Richman
Assistant Examiner—Lyle Aleandary-Alexander
Attorney, Agent, or Firm—Lee C. Robinson

[57] ABSTRACT

A device adapted to generate a gas flow containing a precise amount of impurities. The device comprises a membrane through which an impurity gas peremeates and mixing means to make a mixture of said impurity gas and a vector gas sweeping said membrane. The pressure of said mixture is substantially constant, but adjustable, to enhance the accuracy of the device.

8 Claims, 3 Drawing Sheets

GAS GENERATING DEVICE

BACKGROUND OF THE INVENTION

1. FIELD OF THE INVENTION

This invention relates to gas generating apparatus for calibrating analyzers or the like.

2. DESCRIPTION OF THE PRIOR ART

U.S. Pat. No. 3,856,204 discloses a device for emitting a gas at a constant rate into a moving fluid medium to produce an accurately known concentration of the gas in the said fluid medium. The gas is held in a cylinder under pressure, in equilibrium with its liquid phase or solely in its gaseous phase, and permeates through a permeate material filling an accurately dimensioned passage through one end of the cylinder.

It also discloses the use of such a device with an apparatus for the analysis of fluid mixtures. By injection of an accurate volume of said gas in an accurate volume of fluid medium, it makes it possible to easily calibrate analysers or the like.

An improvement of such a device is disclosed in U.S. Pat. No. 4,399,943. The device of this latter patent comprises two chambers, one for holding the substance in liquefied form and the other for holding it solely in gaseous form. The substance permeates through a permeable material between the two chambers, and then through another quantity of permeable material positioned at the exit from the second chamber.

In both cases, a constant temperature is maintained around the cylinder in order to maintain a constant rate of emission of the substance contained in the said cylinder.

However, though maintaining a constant temperature around the cylinder, it has been discovered that the rate of emission of the substance through the permeable material appeared not to be constant. Having made several measurements with the same fluid medium with an injection through the same passage of the device of the same gas substance, namely water vapor, the inventors found variability of concentrations when compared to a certified calibrated hygrometer. It thus appeared to them that some improvements must be made in such devices to obtain accurate and reproductible results, in order to be able to calibrate any type of analysers, in any conditions.

It is of course well known that there is a need in the semi-conductor industry to accurately measure the concentration of impurities, such as water vapor, in the gases used during manufacture of integrated circuits. Particularly, there is a need to calibrate analysers, such as hygrometers, accurately in the 0.01 to 1.0 ppm range and this need was not fulfilled up to now using the permeation devices disclosed above. These prior art devices are not sufficiently accurate, on the one hand, and they give non reproducible samples, on the other hand.

SUMMARY OF THE INVENTION

According to the invention, the pressure of the vector gas (fluid medium) in which the impurity gas (gas substance) is injected through a membrane, is monitored in order to maintain a constant but adjustable pressure on the side of the membrane which is swept by said vector gas.

It was unexpectedly discovered that when using devices sold for water vapor permeation of the type disclosed in the above U.S. Pat. No. 4,399,942, incorporated herein as a reference, that the pressure of the vector gas which sweeps the permeable material through which said impurity gas permeates, has some influence on the permeation rate of said impurity gas through said membrane. Furthermore, it was assumed that this phenomena may be related to the physical properties of the permeate material and will vary with the flowrate of the sweeping vector gas.

For a given membrane, at a given temperature, the permeation rate P.R. accross the membrane appears to be a linear function of the pressure P of the vector gas:

$$P.R. = A(D) + B(D)33\,P \qquad (1)$$

wherein P=pressure of the vector gas sweeping the membrane A (D) and B (D) are parameters which are dependent on the flowrate D of the vector gas sweeping the membrane.

This resulted in a slight, linear, pressure dependence for the impurity gas concentration generation, according to formula (2), given below.

As some analysers, namely hygrometers, need to be calibrated at a pressure higher than the atmospheric pressure, the correction of the pressure effect makes it is possible to calibrate analysers accurately at about any desired pressure.

The apparatus according to the invention, making use of the various features discovered relating to these membrane permeation devices, makes it possible to calibrate the analysers with various concentrations of impurity gas. This greatly improves the precision of the calibration of the analyser in a wide range of values, avoiding or limiting non-linear effects.

BRIEF DESCRIPTION OF THE DRAWINGS

The invention will be illustrated in more detail by reference to the accompanying drawings, illustrating a preferred embodiment of said invention, wherein.

DESCRIPTION OF A PREFERRED EMBODIMENT

Figure 1:
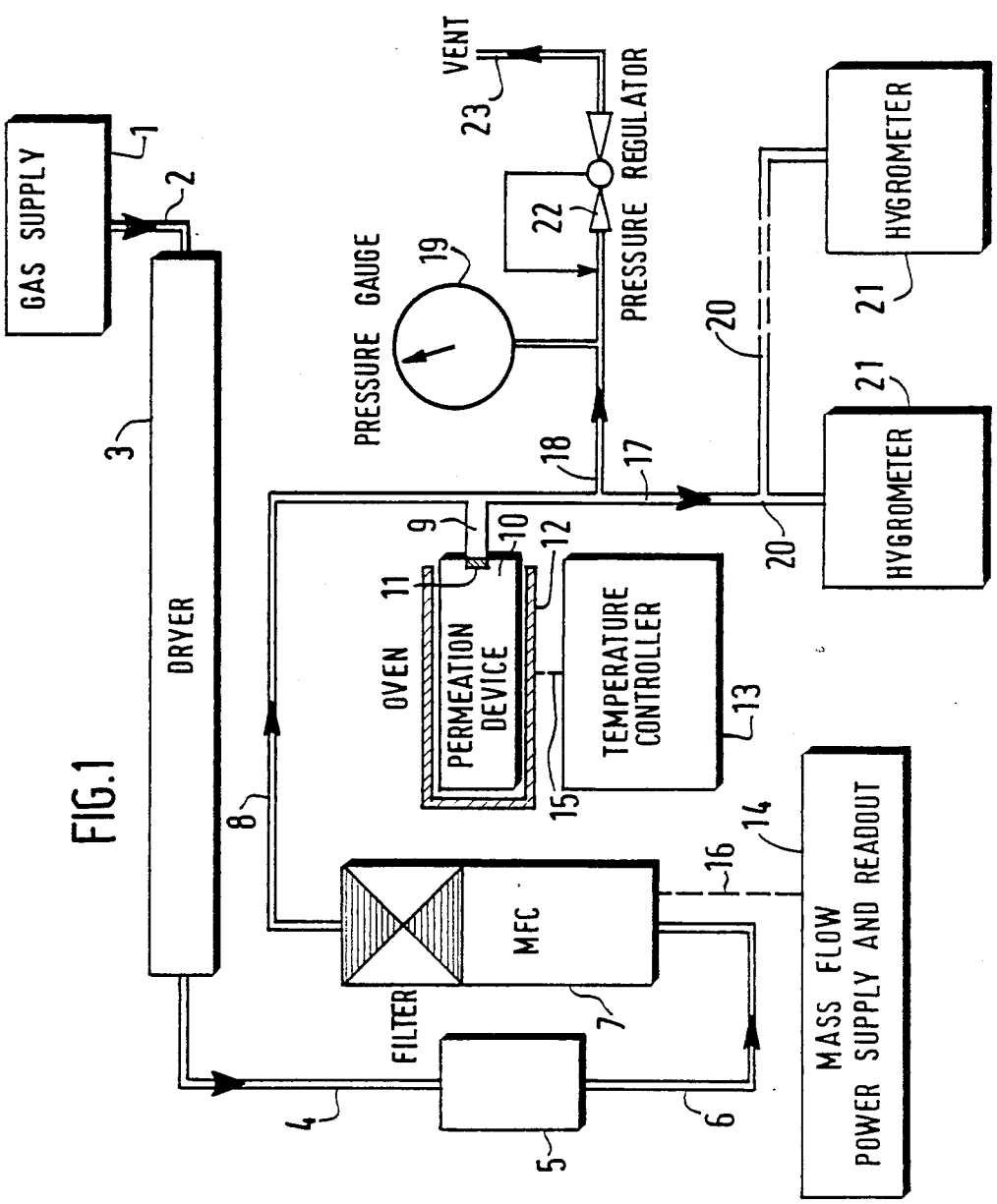
FIG. 1 is a schematic view of an apparatus for calibrating analysers according to the invention.

A stream of gas from gas supply means 1 is injected via duct 2 in a cartridge 3 containing a drying agent (or more generally a scrubber to remove the undesired impurities which may exist in said gas, such as water. The cartridge 3 illustratively is a 9"×½" i.d. cartridge filled with a drying agent, or a 13× or 5 A molecular sieve, activated at elevated temperature to remove all the residual water in it. The gas leaving the dryer 3 through the duct 4 penetrates the filter 5 which is a 2 μm filter used to retain any solid particle escaping from the dryer and hence protect the mass flow controller 7 against plugging. Impurity free gas from the filter 5 is introduced via duct 6 in said mass flow controller 7, which illustratively is of the type sold under the Trademark ALPHAGAZ - 841-09.

The mass flow controller is provided with externally adjustable means in order to deliver a precise flow of gas over the whole range authorized by a given unit.

Said precise flow of impurity free gas is delivered in the duct 8 to which is connected a duct 9 forming a T-junction with said duct 8, said impurity free gas sweeping the membrane 11 of a permeation device 10 sold under the commercial reference G-CAL permeation device by GC Industries, Inc, which permeates water vapor. This device is of the type disclosed in U.S. Pat. No. 4,399,942 with a membrane 11 which is referred to as the first quantity of permeable material, preferably dimethyl-polysiloxane.

As explained in said patent, it is necessary to maintain a substantially constant temperature of the permeation device 10. This is achieved with the oven 12 whose temperature is monitored via the line 15 by the temperature controller 13, sold under the reference OMEGA CN 300 KC by OMEGA Engineering, Inc.

The oven 12 can be simply an aluminum enclosure whose inner diameter is about the outer diameter of the cylindrical permeation device 10, with a heating element such as a belt wrapped around the aluminium cylinder and electrically connected through line 15 to the temperature controller 13. The accurately maintains the outside temperature of the permeation device 10 within a range of 1° C. of the setpoint temperature, which proved to be sufficient to maintain the moisture concentration within a few percent.

It appeared that such a temperature regulation was sufficient to have a measurement of the concentration of water vapor within a few percent relative (in the range 0.01–10 ppm $H_2O$).

The concentration (in the vector gas) of impurity gas which permeates through the membrane device 11 in the T-junction 9 is given by the following formula:

$$C = \frac{K \times PR}{F} \quad (2)$$

wherein

C = concentration of impurity gas in the vector gas (in p.p.m.-volume)

K = molar gas constant at 25° C. (24.45/molecular weight)

PR = permeation rate of the membrane ($10^{-9}$g/minute) at a given temperature

F = gas flowrate (cc/minute)

The gas stream pressure (vector gas) is regulated by an adjustable pressure relief device 22 (pressure regulator), of the typeR3A Series, sold by the Nupro Company. The regulator 22 is connected to duct 8 through duct 18, said pressure being displayed on a pressure gauge 19.

As soon as the pressure of the gas in the duct 8 is higher than a predetermined pressure which is the threshold pressure of the relief valve 22, the mixture of vector gas and impurity gas is vented through the vent 23 until the pressure falls down under said predetermined pressure. The pressure of the mixture (vector and impurity gas) is thus accurately maintained about the said predetermined pressure in the vicinity of the membrane 11.

Figure 2:
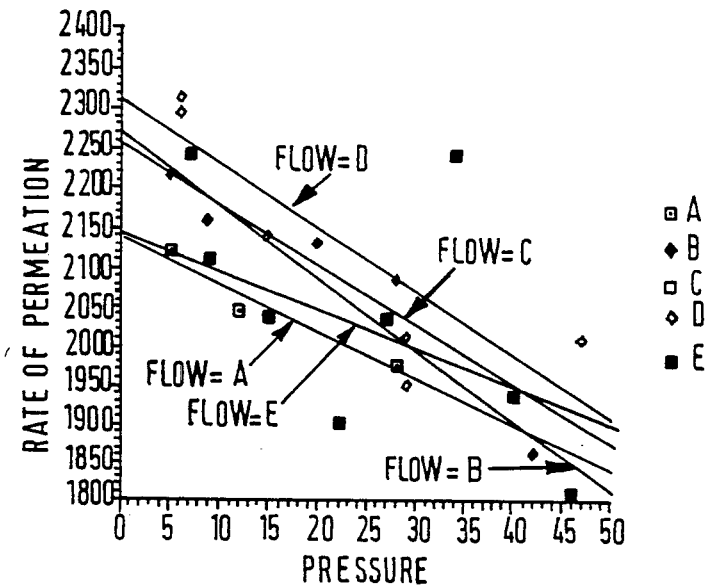
FIG. 2 illustrates the variations of the permeation rate with the pressure, at different flowrates.

Changing the pressure threshold of the pressure regulator 22 makes it possible to modify the pressure of the mixture in the ducts 8, 9, and 17. The duct 17 is adapted to be connected to the apparatus to be calibrated, namely hygrometers like 21, via the ducts 20. FIG. 2 illustrates the variations of permeation rate (P.R.) versus pressure P for different increasing flowrates A < B < C < D < E. The permeation rate is a linear function of the pressure of the gas, whatever the flowrate is, and this permeation rate decreases with the increase of said pressure. The slope is different with different flowrates. These curves examplify the necessity of pressure control on the permeate side of the membrane means.

Figure 3:
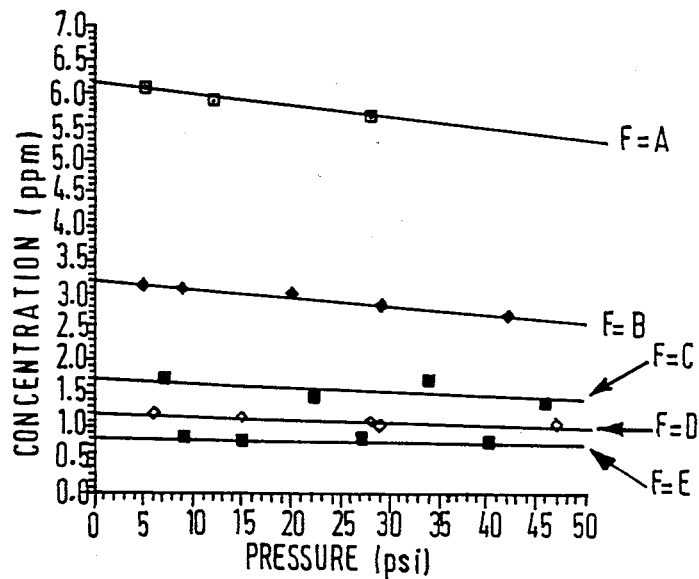
FIG. 3 illustrates the influence of pressure variation on the resulting moisture concentration.

FIG. 3 illustrates the variations of the resulting moisture concentration (ppm) in the mixture versus the pressure on the permeate side of the membrane means. Flowrates are the same as those on FIG. 2. The concentration of the generated moisture decreases with the increase of pressure of the mixture. The slope is decreasing with increasing flowrates.

These curves show that for a precision greater than about five percent, the use of a pressure control system is essential.

Figure 4:
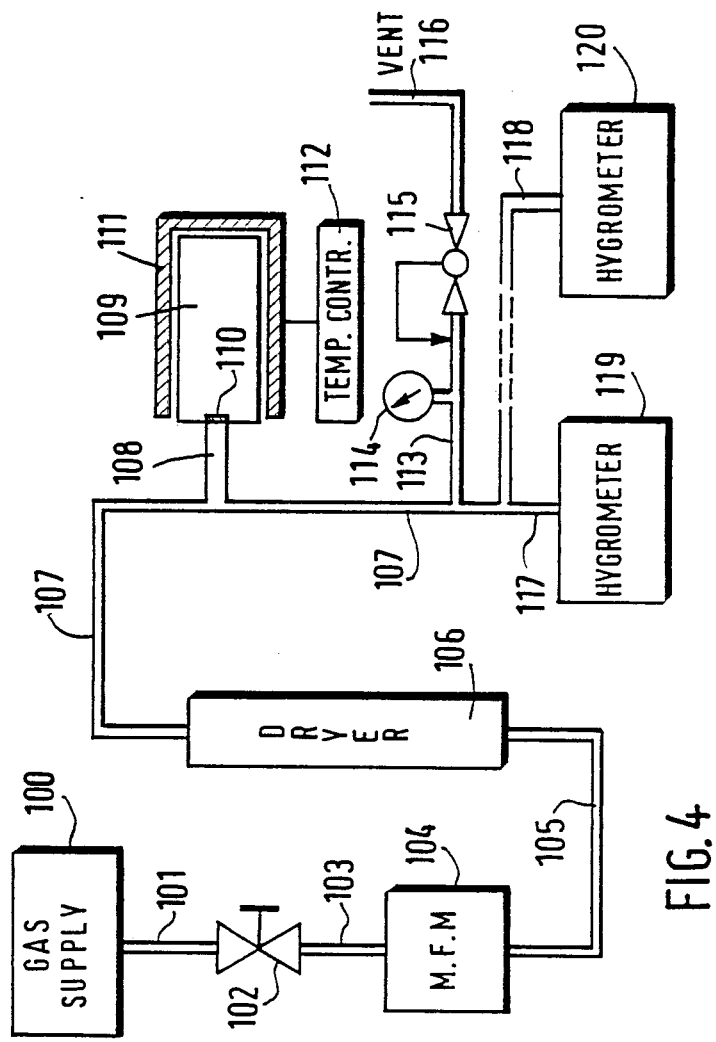
FIG. 4 is a schematic view of calibrating apparatus in accordance with another embodiment of the invention.

FIG. 4 illustrates another embodiment of the invention, having a lower cost than that of FIG. 1, but without automatic regulation of the massic volume of gas.

The stream of gas from gas supply means 100 is sent via duct 101 in a manual valve known as a CONDYNE type 102. On this type of valve, the valve opening is monitored by a 10-turn digital dial. The valve 102 is connected through the duct 103 to a mass flow meter 104 measuring the flow of gas through it. The mass flow meter 104 is connected through the duct 105 to the dryer 106 (or scrubber means when other impurities than moisture have to be extracted from the vector gas) which, in turn, is connected through the ducts 107 and 108 to the permeation device 109 in its oven 111, then to the pressure gauge 114, the pressure regalator 115 and the vent 116 through ducts 107 and 113, and to the hygrometers 119, 120 (or other apparatus) to be calibrated, through ducts 107, 117 and 118. The temperature of the oven 111 is controlled by the temperature controller 112, while the membrane 110 is the permeable membrane as disclosed herein.

The embodiment according to this FIG. 4 provides similar generation of the impurity in the vector gas as the embodiment shown in FIG. 1, but it uses a less precise means of flow control of the gas over the permeation device, in favor of a reduced cost of the apparatus.

We claim:

1. A gas generating device adapted to generate a gas flow containing a precise amount of an impurity gas in a vector gas, said device comprising a scrubber means adapted to receive a stream of vector gas containing gaseous impurities and to deliver the stream free of about any trace of said gaseous impurities, a metering means connected to the scrubber means for receiving said impurity free stream of vector gas therefrom and discharging said impurity free vector gas at a precise massic flowrate, said impurity gas generating means having an output adapted to generate a constant flow of said impurity gas as a function of pressure and temperature, a mixing means adapted to mix said impurity free vector gas and said impurity gas, the mixing means having two inputs and an outlet, a first input connected to the metering means for receiving said impurity free vector gas from said scrubber means, and a second input connected to the impurity generating means, said mixing means delivering a mixture of said impurity free vector gas with a precise amount of said impurity gas to the outlet thereof, a pressure regulator means venting the mixture when the pressure of said mixture is higher than a predetermined adjustable pressure, and at least one gas analyzer connected to the outlet of the mixing means, said impurity generating means comprising membrane means through which the impurity gas permeates, said pressure regulator means maintaining a constant but adjustable pressure on the downstream side of the membrane.

2. A gas generating device according to claim 1, wherein it further comprises temperature regulation means adapted to monitor and maintain the temperature of the impurity generating means within $+1°$ Celcius.

3. A gas generating device according to claim 1 wherein said impurity generating means comprises an enclosure containing said impurity gas, said enclosure having one wall comprising said membrane and adapted to permeate said impurity gas from said enclosure to said mixing means.

4. A gas generating device according to claim 3, wherein said membrane is made of polydimethylsiloxane.

5. A gas generating device according to claim 1, wherein said metering means comprises a mass flow controller means.

6. A gas generating device according to claim 1, wherein said metering means comprises an adjustable valve and a mass flow meter means connected to said valve.

7. A gas generating device according to claim 6, wherein said scrubber means is connected between the mass flow meter means and said first input of said mixing means.

8. A gas generating device comprising, in combination:

a supply of a gas containing gaseous impurities;

a scrubber means for receiving the gas from said supply and removing the gaseous impurities therefrom;

a metering means supplied with the gas from the scrubber means for discharging the gas therefrom at a precise massic flowrate;

a impurity gas generating means having an output for generating a constant flow of a impurity gas as a function of pressure and temperature;

a means for mixing the gases from said metering means and said impurity generating means, the mixing means having two inputs and an outlet, a first input connected to the metering means for receiving the impurity free gas from said scrubber means, and a second input connected to the impurity generating means, said mixing means delivering a mixture of the impurity free gas from said metering means and the impurity gas to the outlet thereof;

a pressure regulator connected to the outlet of the mixing means for venting the mixture when the pressure of said mixture is higher than a predetermined pressure; and at least one gas analyzer connected to the outlet of the mixing means, said impurity generating means comprising a membrane means through which the impurity gas permeates, said pressure regulator maintaining a constant pressure on the downstream side of the membrane.

* * * * *